United States Patent [19]
Mordecki

[11] Patent Number: 4,975,250
[45] Date of Patent: Dec. 4, 1990

[54] ALIGNED SLIDEHOLDER AND ASSEMBLY

[75] Inventor: Thomas A. Mordecki, Monongahela, Pa.

[73] Assignee: Fisher Scientific Co., Pittsburgh, Pa.

[21] Appl. No.: 396,278

[22] Filed: Aug. 21, 1989

[51] Int. Cl.$^5$ .............................. B01L 9/00
[52] U.S. Cl. ........................ 422/99; 422/104; 435/292; 435/310; 211/41; 350/534
[58] Field of Search ............... 422/99, 104, 63, 68, 422/310; 436/180; 435/285, 292, 310; 211/41; 350/534

[56] References Cited

U.S. PATENT DOCUMENTS

| | | | |
|---|---|---|---|
| 3,837,795 | 9/1974 | Becker et al. | 427/4 |
| 4,731,335 | 3/1988 | Brigati | 436/180 |
| 4,777,020 | 10/1988 | Brigati | 422/99 |
| 4,798,706 | 1/1989 | Brigati | 422/102 |
| 4,801,431 | 1/1989 | Cuomo et al. | 422/104 |

FOREIGN PATENT DOCUMENTS 291153 11/1988 European Pat. Off. .

OTHER PUBLICATIONS

"Fisher Histomatic Code-on Series Slide Stainer", Bulletin 885; 7-0319-09, (1987).

Primary Examiner—Robert J. Warden
Assistant Examiner—Lynn M. Kummert
Attorney, Agent, or Firm—Alan M. Doernberg

[57] ABSTRACT

A slideholder device contains a handle portion, a rigid thermoplastic body portion and a plurality of metal clip structures. Each clip structure is received within one of the recesses formed along the interior of a sidewall of the body portion. The body portion forms a first combination of aligning elements to hold each clip structure within a recess. The body portion also has elements to directly align slides, especially in the vertical direction. The holder portion can be attached above one or more than one body portion, and can be detachable. The slide assembly includes a plurality of slide pairs, each extending into opposing recesses on opposite sidewalls of a body portion.

13 Claims, 8 Drawing Sheets

ALIGNED SLIDEHOLDER AND ASSEMBLY

The present invention relates to devices for holding microscope slides in alignment for staining purposes, and especially to devices for holding slide pairs in parallel vertical alignment.

Conventional staining devices hold microscope slides in a parallel array with large horizontal spacings between adjacent slides. See U.S. Pat. No. 3,837,795 to Becker. Precise alignment is not critical for such devices.

A capillary gap staining technology is described in U.S. Pat. No. 4,731,335 to Brigati, where pairs of slides are held in substantially parallel vertical alignment. In the methodologies described in U.S. Pat. No. 4,731,335, vertical alignment between the two slides of a slide pair needs to be maintained, especially at the lower end where the slide pair contacts treating liquid. Furthermore, when an array of multiple slide pairs is used to contact multiple discrete aliquots (droplets) of treating liquid, the horizontal alignment must be maintained as well. Otherwise, some of the slide pairs may not contact the proper droplet at the lower end of the gap (see FIG. 5 of U.S. Pat. No. 4,731,335 and also U.S. Pat. No. 4,798,706 to Brigati, which describes various droplet holders useful in such methodology).

U.S. Pat. No. 4,801,431 to Cuomo and Brigati describes slideholders used to hold multiple slide pairs during the staining method. Particularly in the embodiment shown in FIGS. 2A-2C of that patent, clip structures welded onto a metal plate are used to maintain horizontal alignment, and an alignment strip welded to the same plate is used to maintain vertical alignment. Slideholders of that embodiment have been used commercially with some success. It has been observed, however, that such welding introduces complexity of manufacture, excessive material cost and a great deal of imprecision in alignment, especially horizontal alignment of the slide pairs. The source of that imprecision has been traced to imprecision in positioning the clips onto the metal plate.

BRIEF DESCRIPTION OF THE INVENTION

Improved slideholders have been developed based upon receiving metal clip structures into a chemically resistant molded body structure, which body structure also forms the alignment means for vertically aligning the slide pairs received within the clip structures. Accordingly, the present invention provides a slideholder device comprising:

(a) a handle portion, (b) a rigid thermoplastic body portion, the body portion forming a pair of upstanding sidewalls and a plurality of upstanding recesses spaced along the interior of each sidewall, (c) a plurality of metal clip structures, each clip structure being received within a recess and forming a clip pair for engaging a side of a slide pair, the body portion of the slideholder forming first alignment means for holding each clip structure within a recess and second alignment means for directly engaging each slide pair and aligning the slide pair vertically.

The present invention further provides a slide assembly in which multiple slide pairs are received within such a slideholder. The slide assembly comprises:

(a) a slideholder having:
(i) a handle portion,
(ii) a rigid thermoplastic body portion, the body portion forming a pair of upstanding sidewalls and a plurality of upstanding recesses spaced along the interior of each sidewall, and
(iii) a plurality of metal clip structures, each clip structure being received within a recess and forming a clip pair, and (b) a plurality of slide pairs, each slide pair having one side extending into a recess along one sidewall of the body portion and another side extending into a recess along the other sidewall of the body portion, each of the sides of the slide pair being engaged by a clip pair of a metal clip structure, the body portion of the slideholder forming first alignment means for holding each clip structure within a recess and second alignment means for directly engaging each slide pair and aligning the slide pair vertically.

DETAILED DESCRIPTION OF THE INVENTION

Figures 1A, 1C:
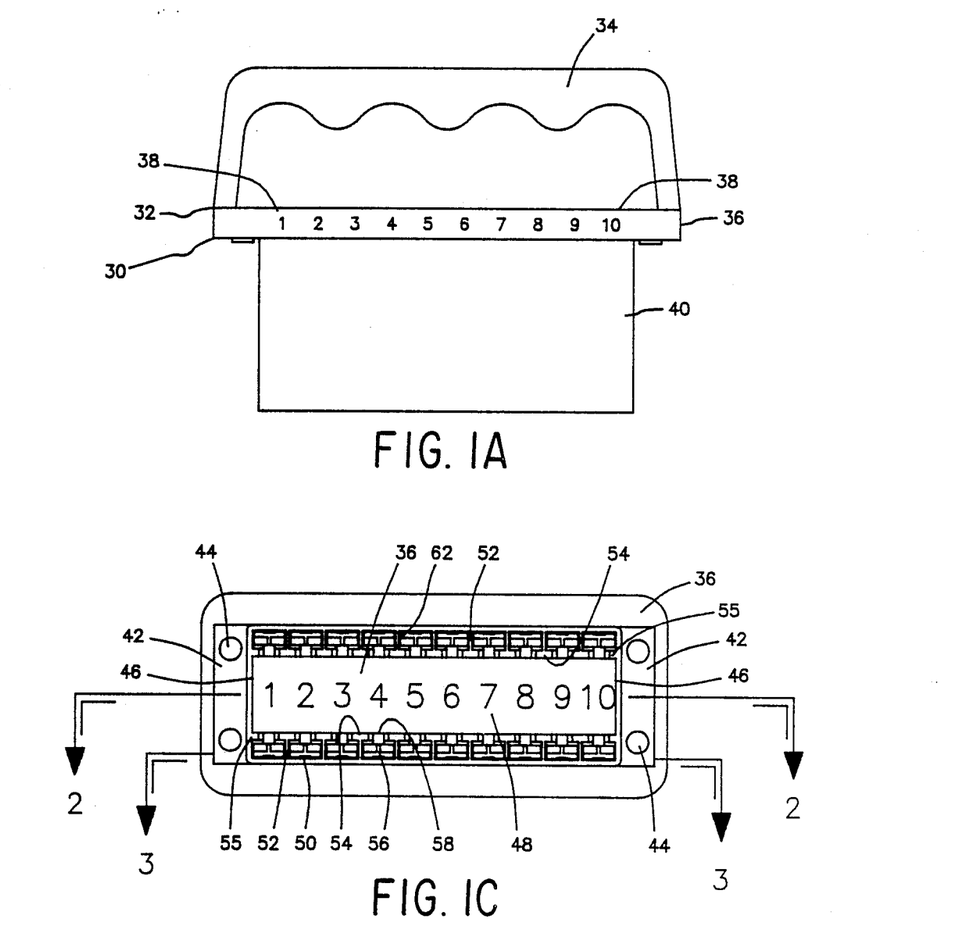
FIG. 1A is an end elevational view of a slideholder 30 according to a first embodiment of the present invention, suitable for holding up to ten slide pairs.
FIG. 1C is a bottom plan view of the slideholder of FIG. 1A.
Figure 1B:
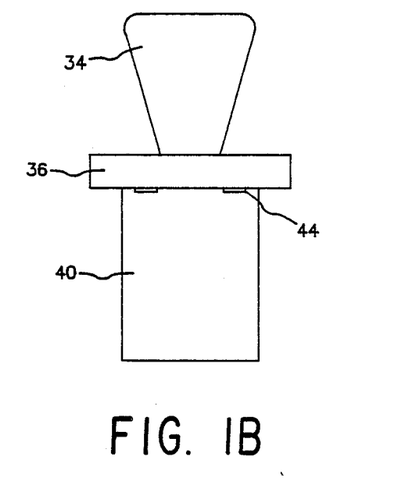
FIG. 1B is a side elevational view of the slideholder of FIG. 1A.

Referring first to FIGS. 1A and 1B, a slideholder 30 is shown suitable for holding up to ten slide pairs in precise alignment. The handle portion 32 of slideholder 30 is formed of a thermoplastic material which is preferably rigid and chemically resistant. Handle portion 32 includes an indented grip portion 34 shaped to be held by hand and a handle base portion 36 which extends horizontally in a rectangular shape. Side markings 38 on base portion 36 identify the locations where slide pairs will be inserted, as described below.

The body portion 40 of slideholder 30 is formed of a thermoplastic material which is rigid and chemically resistant. In general, materials suitable for use as body portion 40 are also suitable for use as handle portion 32. Examples of such materials are the acetal copolymers available under such trademarks as TEXAPOL W2320 (from Texapol Corporation) and CELCON M270 (from Hoechst Celanese Corporation). Materials such as mineral filled polyesters, e.g., VALOX 420 (from General Electric Corporation) may be used for handle portion 32, but may be insufficiently inert (chemically) to be used for body portion 32. Texapol, Celcon and Valox are trademarks of the indicated firms.

Referring now especially to FIG. 1C, the body portion 40 has upper flanges 42 at either end, each forming two through holes (not shown). Projections from the base portion 36 extend downward through these holes and have been heat compressed against flanges 42 to form heat stakes 44, as can be seen in FIGS. 1B and 1C. The body portion 40 forms upstanding endwalls 46 at each end. The underside of the handle base portion 36 is marked with underside markings 48 which correspond to the side markings 38 shown in FIG. 1B. The body portion 40 also forms upstanding exterior sidewalls 50 which, together with upstanding endwalls 46, define a rectangular solid area in front of underside markings 48 in the view of FIG. 1C (below the underside markings 48 when the slideholder 30 is upright).

Extending inward from the exterior sidewalls 50 are a series of upstanding dividers or ribs 52, each forming a right angle to the sidewall 50. Interior of and connected to (i.e., integral with) each rib 52 is an upstanding interior wallpost or retainer 54 at right angles to the ribs 52 and parallel to the sidewall 50. Since slideholder 30 is designed for up to ten slide pairs, there are nine ribs 52 on each of the two sidewalls 50 and a total of eighteen retainers 54. There are also four half-retainers 55 aligned with retainers 54 and extending inward from the two endwalls 46.

The body portion 40 therefore defines two rows of ten recesses 56. Each recess 56, except for the four end recesses, is surrounded by a sidewall 50, two ribs 52 and two retainers 54, except for a channel 58 extending toward the interior between the two retainers 54. See also FIG. 1D. Each of the four end recesses 56 is surrounded by a sidewall 50, an endwall 46, a retainer 54 and a half-retainer 55, except for a channel 58 extending toward the interior between the retainer 54 and the half-retainer 55. Each channel 58 along one sidewall 50 is aligned with a corresponding channel 58 along the other sidewall 50, and one of the underside markings 48 is generally aligned with that pair of channels 58. As described below, that pair of channels 58 helps define the horizontal alignment of a slide pair.

Figure 1D:
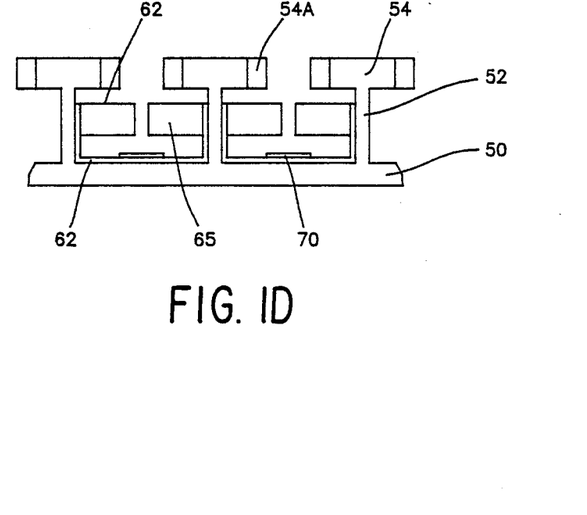
FIG. 1D is an enlarged bottom plan view of a portion of the slideholder of FIG. 1A.

Referring to FIGS. 1C and 1D, a clip structure 62 is received within each of the twenty recesses 56. As seen in FIG. 1D, a lower clip pair 65 is aligned within each recess 56 to form a space for receiving a slidepair which extends laterally through each channel 58. In FIG. 1D, the sidewall 50, ribs 52 and retainers 54 as described above can also be seen. The locking tab 70 serves to hold clip structure in place vertically as described below in connection with FIG. 4.

Figure 2:
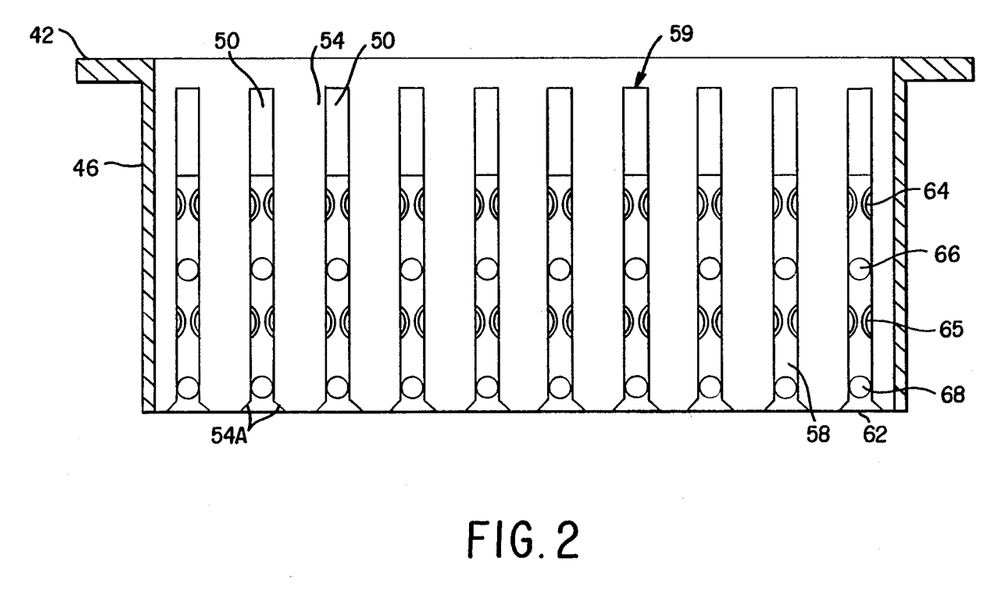
FIG. 2 is an enlarged side elevational view taken in section along line 2—2 in FIG. 1C.

Referring now to FIG. 2, the configuration of the retainers 54 and channels 58 along one sidewall 50 is shown. Each channel 58 extends vertically upward in a rectangular shape, except for a flared out lower end formed by chamfers 54a in the retainers 54. The top horizontal edge of each channel 58 is designated as 59 in FIG. 2. The width of each channel 58 (e.g., 2.4 mm) is equal to or slightly larger than the expected thickness of the slide pair to be fitted within the channel 58. The flare at the lower end of each channel 58 helps direct a slidepair into the channel 58. Clip structures 62, formed of a resilient metal material such as stainless steel or phosphor bronze, can be seen in FIG. 2 behind each channel 58.

Figure 3:
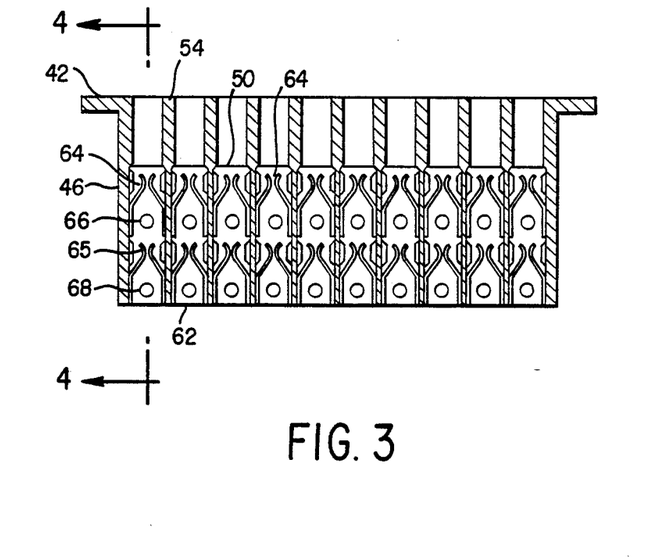
FIG. 3 is a side elevational view taken in section along line 3—3 in FIG. 1C.

Referring now to FIG. 3, each clip structure 62 can be seen either between two ribs 52 or between a rib 52 and an endwall 46. Metal clip structure 62 can be any of the commercially available devices widely used for holding printed circuit boards in place, such as those available from Unitrac division of Calabro Industries. Each clip structure 62 is provided with an upper clip pair 64 and a lower clip pair 65 and with an upper welding hole 66 and a lower welding hole 68. Such welding holes are used in the device shown in U.S. Pat. No. 4,801,431 to weld the clip structure to a metal plate. In the present embodiment, the lower welding hole is not used at all. The upper welding hole 66 engages a locking tab 70, as shown in FIG. 4, and as described more completely below in connection with the assembly of the slideholder 30.

To assemble the slideholder 30, one starts with the handle portion 32 as one molded part, the body portion 40 as a second molded part and twenty clip structures 62. The handle portion 32 can be attached to body portion 40 by heat compressing heat stakes 44 through flange portion 42 either before or, preferably, after the insertion of clip structures 62. Body portion 40 without handle portion 32 forms a flat upper surface. The inverted body portion 40 can be supported by a flat tabletop on that surface during vertical insertion of the clip structures 62.

Each clip structure 62 is inserted into a recess 58. The various structures around the recess 58, and especially ribs 52 and retainers 54 align the clip structure 62 horizontally (see especially FIG. 1D) as it is inserted vertically into the recess 58. As best seen in FIG. 4, the ramp shape of locking tab 70 on sidewall 50 permits the top of the clip structure 62 to move vertically until locking tab 70 snaps inwardly through upper welding hole 66. As seen in FIG. 4, however, the more lateral top surface of locking tab 70 engages a surface at upper welding hole 66 and prevents the clip structure 62 from being withdrawn from recess 56. These structures together serve as the first alignment means to hold the clip structure 62 in precise horizontal alignment along the sidewall 50.

Figure 4:
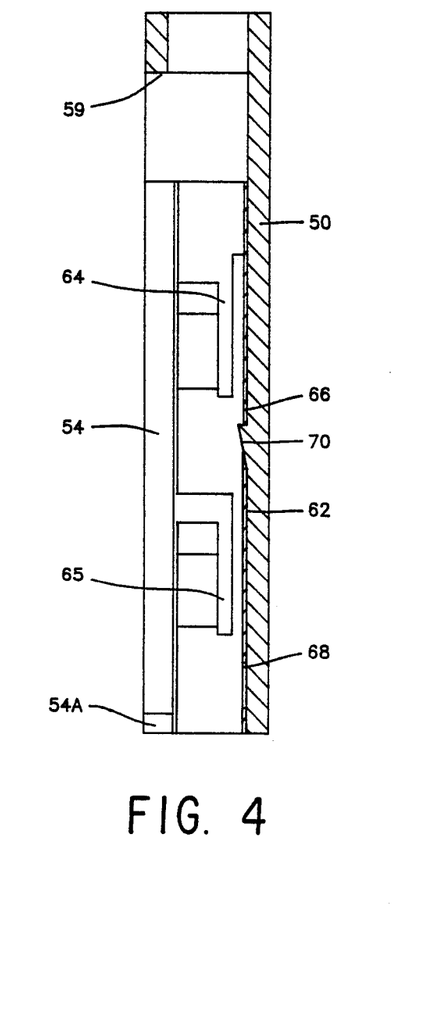
FIG. 4 is an enlarged end elevational view taken in section along line 4—4 in FIG. 3.

In FIG. 4, parts numbered 50, 54, 54a, 59, 62, 64 and 66 are each items discussed above in connection with previous FIGS.. They are referenced in the enlarged cross-section of FIG. 4 in order to show how various parts cooperate to form the first alignment means and to hold clip structure 62 in place.

Once the slideholder 30 is fully assembled, slidepairs can now be inserted. Suitable slides already have a shim or pair of abutting painted surfaces to define a capillary gap between the two slides of the slide pair. See U.S. Pat. Nos. 4,731,335 and 4,777,020 and copending U.S. patent application Nos. 112,404, filed Oct. 26, 1987 (corresponding to EP-A-0,291,153) and 253,134, filed Oct. 4, 1988. U.S. Ser. No. 253,134 is copending and commonly-assigned. The present assignee is co-assignee of U.S. Ser. No. 112,404.

Each side of each slide pair is received within a recess 56 along one sidewall 50. The other side of the same slide pair is received within the corresponding recess 56 along the other sidewall 50. Referring to FIG. 1C, it can be seen that there is a channel 58 on either side of each underside marking 48. The slide pair corresponding to that underside marking will have one side received within one of those two channels 58 and the opposite side received within the other of those two channels 58. See also FIG. 1D.

The shape of each channel 58 defined by the retainers 54 can be seen in FIGS. 1D and 2 to guide the end of the slidepair centrally within the recess 56 and into the interior of first the lower clip pair 65 and then the upper clip pair 64. The spring force of the clip pairs 64 and 65 serves to compress the slides of a slide pair against the shim or painted surface to define the capillary gap. The precise horizontal alignment of the slide pair is maintained both by the clip pairs 64 and 65 and by the retainers 54.

Each slide pair moves upwardly in the channel 58 until it engages the horizontal surface 59. This surface aligns the two slides of the slide pair vertically, both when the slide pair is inserted and each time the slide pair is pressed upwardly (as when the slidepair contacts a droplet holder). Such surface 59 forms an additional portion of the second alignment means to align the slide pair. By having channels 58 acting to align the slide pairs both horizontally and vertically, body section 40 is not totally dependent upon clip pairs 64 and 65 to align the slide pairs. By contrast, in U.S. Pat. No. 4,801,431, alignment of the slide pairs was dependent solely upon clips spot welded to a metal plate and upon alignment strip 156 (of FIG. 3C of that patent), also spot welded to the metal plate. Furthermore, alignment strip 156 could align the slide pairs vertically only if they were aligned horizontally by the clips in a proper fashion.

While the dimensions selected for various elements of the slideholder 30 can be varied between specific embodiments, many of the specific dimensions of particular embodiments are controlled within close tolerances, especially at the minimum end. Representative dimensions for a particular embodiment, as illustrated in FIGS. 1A-4, are as follows. Channel 58 (see FIG. 2) is 2.4-2.6 mm wide and 35 mm high (from top surface 59 to the base of retainers 54). The dimensions of each recess 56 (as seen in FIG. 1D) are 7.1-7.4 mm wide (between the facing surfaces of adjacent ribs 52) and 3.9-4.2 mm deep (between the surface of retainer 54 and the projecting surface of locking clip 70). The total lateral dimension of the holder (from the projecting surface of locking clip 70 from a recess 56 on one sidewall 50 to the projecting surface of locking clip 70 from a recess 56 on the other sidewall 50) is 26 mm. This lateral dimension is suitable both for standard metric slides (75 mm by 25 mm) and three inch by one inch slides (76.2 mm by 25.4 mm). Various other dimensions can be seen from the various drawings by comparing the particular dimension to one of the above dimensions (assuming the drawings are to scale). Depending upon the dimensions and numbers of slides to be used, each of the above dimensions can be modified accordingly.

Figure 5:
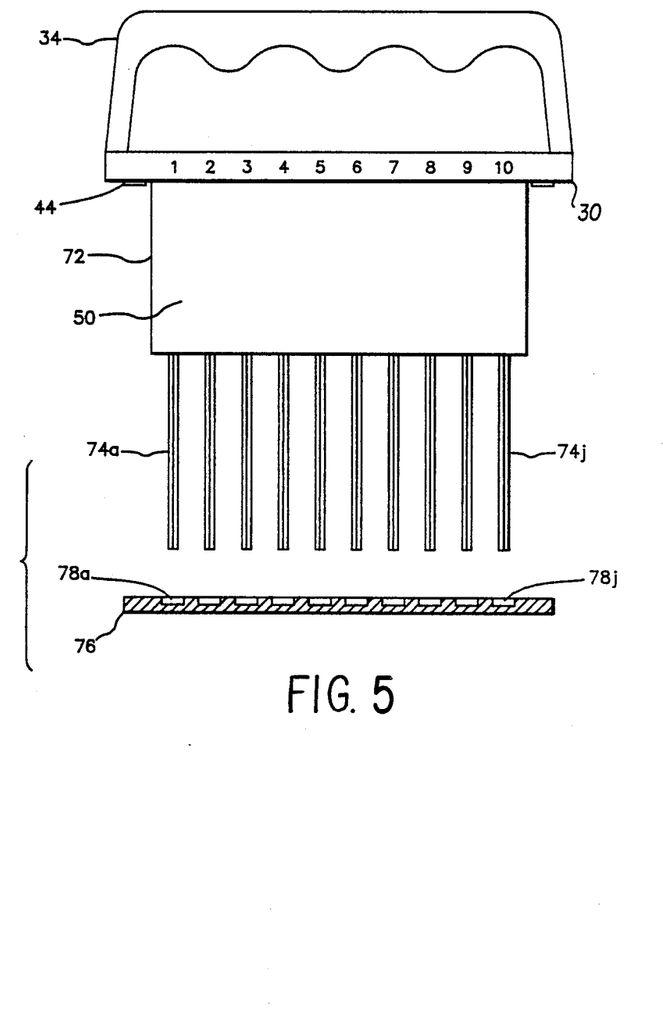
FIG. 5 is a side elevational view of a slide assembly consisting of the slideholder of the previous FIGS. filled with ten slide pairs in use.

FIG. 5 shows ten slide pairs 74a through 74j extending downwardly from body portion 40 of slideholder 30 after being inserted in the fashion described above. Grip portion 34 can be used to move that slide array from one station to another, with each station containing either a treating liquid, a blotter or an incubation device, as described more fully in U.S. Pat. No. 4,731,335. Shown in FIG. 5 is an example of a station when ten droplets are supported by a droplet holder 76 (available from Fisher Scientific Company as an ISOLON device, see U.S. Pat. No. 4,798,706) which has ten holes 78a through 78j. As indicated in FIG. 3A of U.S. Pat. No. 4,798,706, the holes can be caplet shaped in cross-section and arranged in three rows of ten with suitable indicia ("1" through "10" to indicate the holes, "A" through "C" to indicate the rows). Because slideholder 30 holds each slide pair 74a through 74j in precise horizontal alignment, the base of each slide pair can contact the liquid in a separate hole. It will be appreciated that holes 78a through 78j may, in particular stations such as the primary antibody station, actually contain ten different treating reagents. The precise vertical alignment assures that both slides of a slide pair are aligned at their bottom edge to improve the capillary action drawing liquid into a slide pair. The precise vertical alignment between the ten slide pairs 74a through 74j assures that all ten slide pairs can contact the droplet holder evenly and simultaneously. Even if one lowers the slideholder 30 at a slight angle to the vertical, the planar array formed by the ten lower ends of the slide pairs can be tilted onto the planar surface of the dropletholder 76. In that fashion, all ten capillary gaps can be given an opportunity to be filled with treating liquid.

Using the slideholder 30 described above, only one row of ten holes of dropletholder 76 is used in a single step. One can, in fact, use the same dropletholder 76 for two steps (using rows A and C for example) or for three steps (using rows A, B and C, see FIG. 3A of U.S. Pat. No. 4,798,706).

Figure 6:
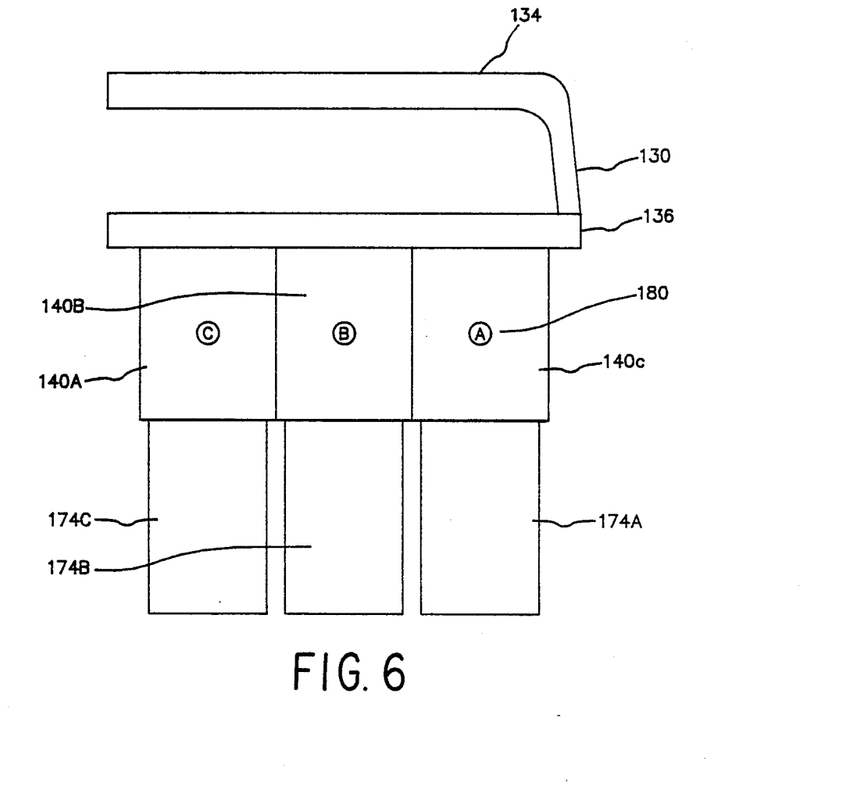
FIG. 6 is an end elevational view similar to FIG. 1B, of a slideholder 130 according to a second embodiment of the present invention, suitable for holding up to thirty slide pairs.

FIG. 6 illustrates a modified slideholder 130 suitable for holding up to thirty slide pairs in precise alignment. Indented grip portion 134 is similar to grip portion 34 in the first embodiment, but can be larger. Handle base portion 136 is similar to base portion 36 of the first embodiment in thickness and length, but is wider (for example 2.5 times as wide) and is molded with twelve rather than four projections for forming heat stakes. Three body portions 140A, 140B and 140C are each substantially identical to body portion 40 of the first embodiment, except that each bears an end marking 180 ("A", "B" or "C") which can correspond to the row markings on the droplet holder (see FIG. 3A of U.S. Pat. No. 4,798,706).

Slideholder 130 can be assembled in similar fashion to slideholder 30. In general, twenty clip structures can be inserted into each body portion 140A, 140B and 140C. Then the three assemblies can be fitted onto handle portion 136 and the heat stakes formed Slide pairs (up to thirty) can then be inserted, used and removed.

Alternatively, each body portion 140A, 140B and 140C can be attached to handle portion 136 in a reversible fashion such as by having the projections from the handle portion through the holes in the upper flanges of each body portion be reversibly engaged by a locking clip rather than being compressed to form a heat stake. In such case, one can load each body portion with slide pairs separately and then attach and clip the body portions 140A, 140B and 140C, each filled with slide pairs to the handle portion 136. Such an arrangement facilitates loading of slide pairs, especially into middle body portion 140B, and can be used in environments where body portion 140A, 140B and 140C are loaded in one or more laboratories different from the laboratory in which staining is to be conducted.

The fact that the body portions (40, 140A, 140B and 140C) and handle portions (32 and 134/136) are produced from thermoplastic material by molding facilitates reproducibility between parts. Combined with the first and second alignment means that the body portions define (as described above), the reproducibility between parts enables various body portions to be interchangeably assembled with various handle structures.

The above two embodiments both employ rows of ten slide pairs to coincide with the ISOLON devices now available. It should be appreciated, however, that the present invention can be applied equally to shorter or longer rows of slide pairs, or to various numbers and arrangements of such rows. Furthermore, the slideholders and slide assemblies may have various shim arrangements or painted surfaces, and may have plain glass surfaces within each capillary gap or various other surfaces (e.g., adsorbent surfaces, see U.S. Ser. No. 253,134, referenced above) depending upon the application.

Other geometries can be formed by the body members to define the interior recesses and to form the first alignment means for holding the clip structures and second alignment means for directly aligning the slide pairs. For example, the first alignment means could also be obtained by (1) using two locking tabs similar to element 70 that would provide alignment of the clip structures while also securing them to the sidewall or (2) providing short horizontal rib structures that would engage the clip structures on the top and bottom instead of on the side, or (3) having protrusions from the ribs 52 engage a portion of the sides of the clip structures instead of the ribs 52 engaging the sides of the clip structures along their full height. The recesses 56 could also be formed in the sidewalls along less than the full height of the sidewalls, leaving for example a ledge above the recess which engages the top of the slip structures.

The second alignment means could also include such a ledge on the top of each recess 56 to engage the top of the slides. The channel 58 or at least the portion acting as surface 59 could be formed by a structure integral with the clip structure 62 rather than being formed by retainers 54. Retainers 54 could also form channels 58 of a different shape, especially above the height of lower clip 65.

One or more of the above modifications in the exemplary embodiment can be made, so long as adequate first alignment means are provided to align each clip structure within a recess and adequate second alignment means are provided to cooperate with the clip structures in aligning slides which are inserted into the slideholder. It is further contemplated, although not preferred, that structures not associated with the body portion, as for example a ledge formed by the handle portion, could perform some or all of these two aligning functions.

The slideholder of the present invention is distinguished from that of U.S. Pat. No. 4,801,431 in that the body structure of the present slideholder forms recesses and forms both the first and second alignment means, rather than relying upon assembly precision to align the clip structures.

What is claimed is:

1. A slideholder device comprising:
   (a) a handle portion,
   (b) a rigid thermoplastic body portion, the body portion forming a pair of upstanding sidewall and a plurality of upstanding recesses spaced along the interior of each sidewall,
   (c) a plurality of metal clip structures, each clip structure being received within a recess and forming a clip pair for engaging a side of a slide pair,
   the body portion of the slideholder forming first alignment means for holding each clip structure within a recess and second alignment means for directly engaging and aligning a slide pair vertically.

2. The slideholder device of claim 1 wherein each clip structure forms an upper clip pair and a lower clip pair.

3. The slideholder device of claim 1 wherein the body portion further defines a pair of upstanding endwalls, wherein the first alignment means comprises a plurality of ribs formed by the body portion extending inwardly from each of the sidewalls, each non-end clip structure being engaged by an adjacent pair of ribs and each end clip structure being engaged by an endwall and the rib adjacent to the endwall.

4. The slideholder device of claim 3 wherein the body portion further defines a plurality of retainers, each retainer extending from a rib in a direction substantially parallel to a sidewall, the first alignment means further comprising one of the retainers, engaging each clip structure in a horizontal direction lateral to the ribs and opposite to the adjacent sidewall.

5. The slideholder device of claim 3 wherein each metal clip structure defines a through-hole, wherein the first alignment means comprises a projection extending inwardly from the sidewall within each recess and wherein each of the projections is received within the through-hole of the metal clip structure in the recess.

6. The slideholder device of claim 5 wherein each metal clip structure forms an upper clip pair above the through-hole and a lower clip pair below the through-hole.

7. The slideholder device of claim 1 wherein each metal clip structure forms an upper clip pair and a lower clip pair.

8. A slide assembly comprises:
   (a) a slideholder having:
      (i) a handle portion,
      (ii) a rigid thermoplastic body portion, the body portion forming a pair of upstanding sidewalls and a plurality of upstanding recesses spaced along the interior of each sidewall, and
      (iii) a plurality of metal clip structures, each clip structure being received within a recess and forming a clip pair, and
   (b) a plurality of slide pairs, each slide pair having one side extending into a recess along one sidewall of the body portion and another side extending into a recess along the other sidewall of the body portion, each of the sides of the slide pair being engaged by a clip pair of a metal clip structure,
   the body portion of the slideholder forming first alignment means for holding each clip within a recess and second alignment means for directly engaging each slide pair and aligning the slide pair vertically.

9. The slide assembly of claim 8 wherein each metal clip structure forms an upper clip pair which engages one side of a slide pair near the top of the slide pair and a lower clip pair which engages the one side of the same slide pair near the middle of the slide pair.

10. The slide assembly of claim 9 wherein the metal clip structure defines a through hole above the lower clip pair and below the upper clip pair, and wherein the first alignment means comprises a projection extending inwardly from the sidewall within each recess, and wherein the projection is received within the through-hole.

11. The slide assembly of claim 8 wherein the handle portion is attached above the body portion.

12. The slide assembly of claim 8 wherein the handle portion is attached above a second plurality of body portions, each of the second plurality of body portions holding a first plurality of slide pairs.

13. The slide assembly of claim 12 wherein each of the second plurality of body portions is removably attached to the handle portion.

* * * * *